(12) United States Patent
Isaev et al.

(10) Patent No.: US 9,745,337 B2
(45) Date of Patent: Aug. 29, 2017

(54) COMPLEX COMPOUNDS OF GERMANIUM, METHODS FOR PRODUCING SAME, AND DRUGS

(71) Applicant: OBSCHESTVO S OGANICHENNOI OTVETSTVENNOSTYU "WDS FARMA", Moscow (RU)

(72) Inventors: Alexandr Dmitrievich Isaev, Moscow (RU); Igor Valerievich Ambrosov, Moscow (RU); Tamaz Omarovich Manasherov, Moscow (RU); Svetlana Konstantinovna Matelo, Mechnikovo (RU)

(73) Assignee: OBSCHESNO S OGRANICHENNOI OTVETSTVENNOSTYU "WDS FARMA", Moscow (RU)

( * ) Notice: Subject to any disclaimer, the term of this patent is extended or adjusted under 35 U.S.C. 154(b) by 214 days.

(21) Appl. No.: 14/400,081

(22) PCT Filed: Nov. 1, 2012

(86) PCT No.: PCT/RU2012/000897
§ 371 (c)(1),
(2) Date: Nov. 10, 2014

(87) PCT Pub. No.: WO2013/172732
PCT Pub. Date: Nov. 21, 2013

(65) Prior Publication Data
US 2015/0126726 A1     May 7, 2015

(30) Foreign Application Priority Data
May 16, 2012  (RU) ................................ 2012120329

(51) Int. Cl.
| | | |
|---|---|---|
| *C07H 19/167* | (2006.01) | |
| *C07H 19/173* | (2006.01) | |
| *C07F 1/00* | (2006.01) | |
| *C07F 3/00* | (2006.01) | |
| *C07F 3/08* | (2006.01) | |
| *C07F 5/00* | (2006.01) | |
| *C07F 5/06* | (2006.01) | |
| *C07F 7/00* | (2006.01) | |
| *C07F 9/00* | (2006.01) | |
| *C07F 11/00* | (2006.01) | |
| *C07F 13/00* | (2006.01) | |
| *C07F 15/00* | (2006.01) | |

(Continued)

(52) U.S. Cl.
CPC ....... *C07H 23/00* (2013.01); *A61K 47/48015* (2013.01); *A61K 47/48038* (2013.01); *C07F 7/30* (2013.01)

(58) Field of Classification Search
CPC ..... C07F 7/30; C07H 23/00; A61K 47/48038; A61K 47/48015
See application file for complete search history.

(56) References Cited

U.S. PATENT DOCUMENTS 3,616,208 A * 10/1971 Howells ................. C07H 19/16
435/88
3,674,823 A 7/1972 Makabe
(Continued)

FOREIGN PATENT DOCUMENTS

CN  1154359 A   7/1997
DE  3212817 A1  10/1983
(Continued)

OTHER PUBLICATIONS

Manuel Cotarelo, Pilar Catalán, Carlos Sánchez-Carrillo, Ana Mennasalvas, Emilia Cercenado, Antonio Tenorio and Emilio Bouza, "Cytopathic effect inhibition assay for determining the in vitro susceptibility of herpes simplex virus to antiviral agents," Journal of Antimicrobial Chemotherapy, 1999, vol. 44, pp. 705-708.

(Continued)

*Primary Examiner* — Lawrence E Crane
(74) *Attorney, Agent, or Firm* — Ladas & Parry LLP

(57) ABSTRACT

The invention relates to the development of drugs intended for the prophylaxis and/or treatment of viral diseases caused, in particular, by herpes viruses. What are proposed are complex compounds of germanium having the general structural formula:

$$Ge_x[AD][CA]_y[AA]_z \quad (1),$$

Figure 1:
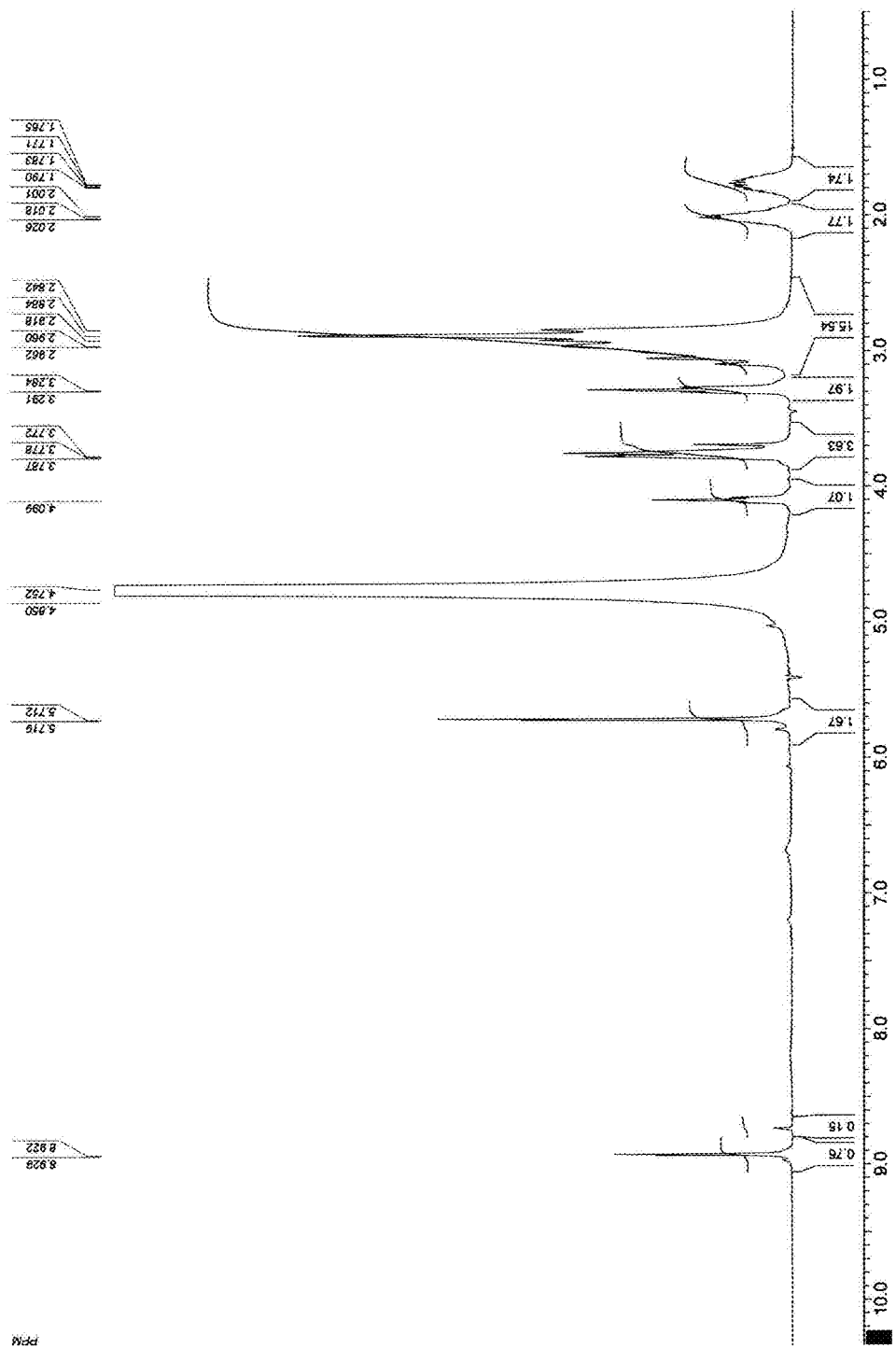

where AD is a derivative of a nitrogenous base of the purine series that has antiviral activity and can be selected from guanine derivatives, such as acyclovir, valacyclovir, gancyclovir and pencyclovir, or from adenine derivatives, such as vidarabine; CA is a hydroxycarboxylic acid which can be selected from acids such as (but not limited to) citric acid, lactic acid and malic acid; AA is an amino acid which can be selected from various a-amino acids, such as arginine, gylcine, lysine and threonine, and where x=1-2, y=2-4 and z=0-2. Complex compounds of germanium have a high level of antiviral and immune-stimulating activity and are readily soluble in water. The above mentioned compounds are produced by producing an aqueous suspension of germanium dioxide, adding a hydroxycarboxylic acid, a derivative of a nitrogenous base of the purine series and, optionally, but preferably, an amino acid thereto, heating the mixture produced at a temperature of 40-100° C. for 3-14 hours while stirring and removing the water from the solution, thus producing a complex compound of germanium.

11 Claims, 7 Drawing Sheets

(51) Int. Cl.
*C07H 23/00* (2006.01)
*C07F 7/30* (2006.01)
*A61K 47/48* (2006.01)
*C07F 17/00* (2006.01)

(56) References Cited

U.S. PATENT DOCUMENTS

| | | | |
|---|---|---|---|
| 6,448,227 | B1 | 9/2002 | Treusch |
| 9,546,188 | B2 * | 1/2017 | Isaev .................. C07F 7/30 |
| 2015/0011523 | A1 * | 1/2015 | Isaev .................. C07F 7/30 |
| | | | 514/188 |

FOREIGN PATENT DOCUMENTS

| | | |
|---|---|---|
| DE | 103 43 365 A1 | 4/2005 |
| EP | 0 477 871 A2 | 4/1992 |
| JP | 49-24213 A | 3/1974 |
| RU | 2 233 280 C2 | 7/2004 |
| RU | 2 240 792 C2 | 11/2004 |
| RU | 2 104 032 C1 | 2/2008 |
| WO | 98/09975 A1 | 3/1998 |
| WO | 00/10561 A1 | 3/2000 |

OTHER PUBLICATIONS

J. P. Kruppenbacher, R. Klāss, R., and H. J. Eggers, "A rapid and reliable assay for testing acyclovir sensitivity of clinical herpes simplex virus isolates independent of virus dose and reading time," Antiviral Research, 1994, vol. 23, pp. 11-22.

S.J. Flint, L. W. Enquist, V. R. Racanielle, and A. M. Skalka, "Virological Methods" in Principles of Virology, ASM Press); 2009.

L.J. Reed, and H.Muench, "A simple method of estimating fifty percent endpoints," The American Journal of Hygiene 1938, 27: 493-497.

Herbert E. Kaufman, M.D., Eeva-Lisa Martola, M.D., and Claes Dohlman, M. D., "The use of 5-iodo-2'-deoxyuridine (IDU) in the treatment of herpes simplex keratitis," Arch. Opthalmol. 1962; 68:235-239.

William J. Mason, M.D. and Hilary H. Nickols, M.D., "Crystalluria from acyclovir use," N. Engl. J. Med. 358:13, Mar. 27, 2008.

Gus'kova, T.A., Nikolaeva, I.S., and Peters, V.V., "Methodological Guidance to Study Antiviral Activity of Pharmacological Agents" in "The Manual on the Experimental (Preclinical) Study of New Pharmacological Agents," Moscow, Ministry of Public Healthcare of the Russian Federation, Remedium IPA, CJSC, 2000, pp. 274-280.

Espacenet English abstract of CN 1154359 A, Jul. 16, 1997.

* cited by examiner

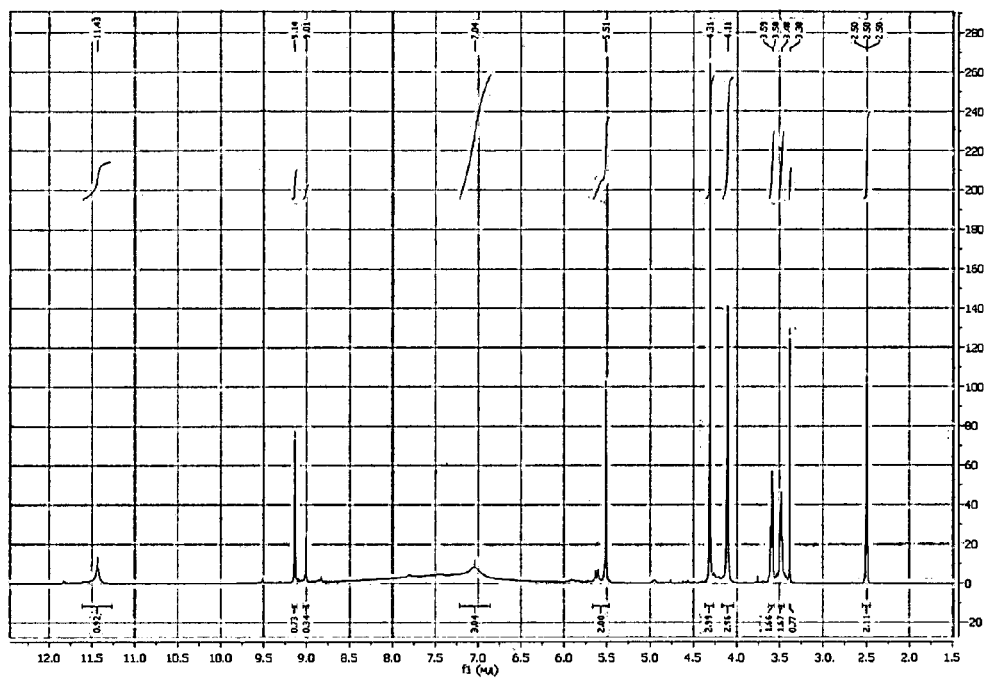
Fig. 6. ¹H NMR spectrum (DMSO-d₆) for the germanium complex compound with tartaric acid and acyclovir
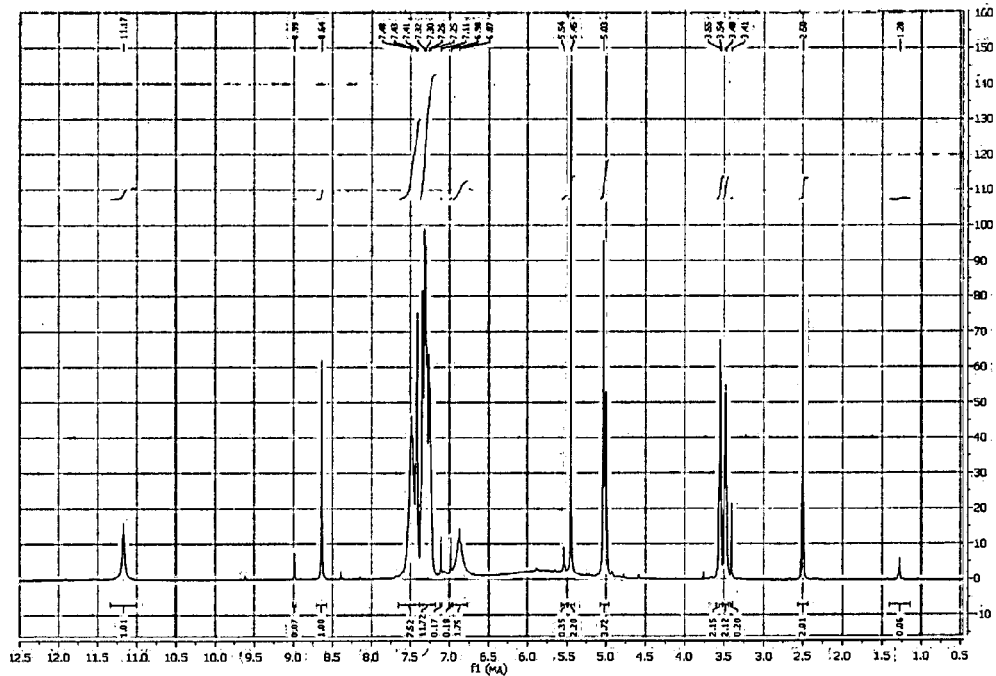
Fig. 7. ¹H NMR spectrum (DMSO-d₆) for the germanium complex compound with mandelic acid acid and acyclovir

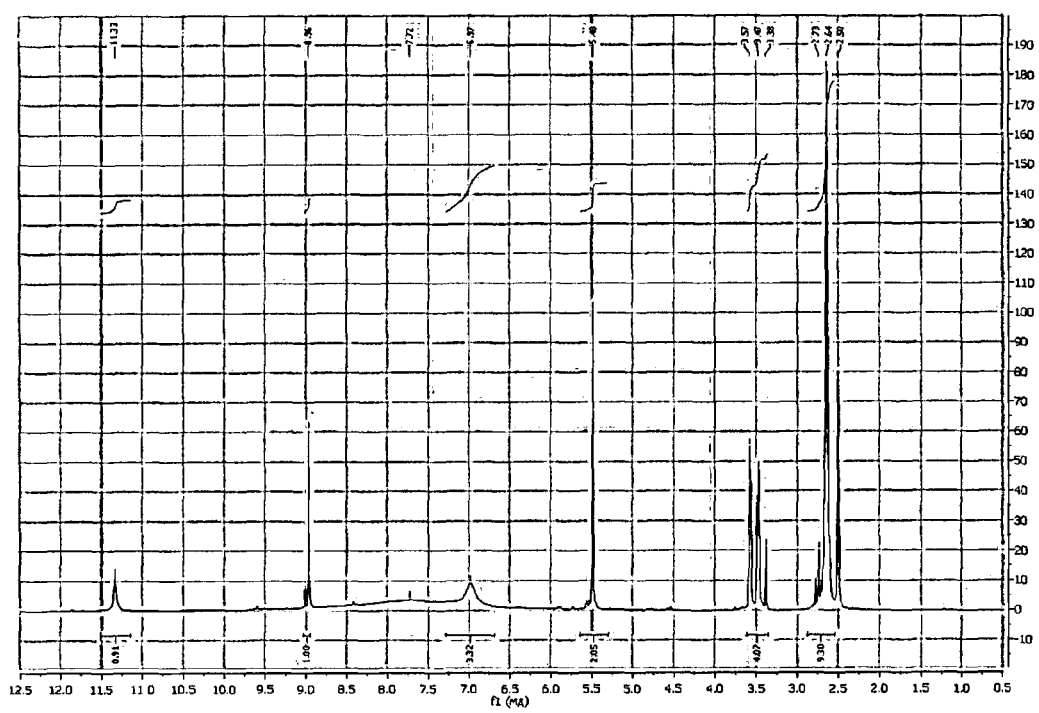
Fig. 8. ¹H NMR spectrum (DMSO-d₆) for the germanium complex compound with citric acid and acyclovir

COMPLEX COMPOUNDS OF GERMANIUM, METHODS FOR PRODUCING SAME, AND DRUGS

RELATED APPLICATION INFORMATION

This application is a 371 of International Application PCT/RU2012/000897 filed Nov. 1, 2012 entitled "Complex Compounds Of Germanium. Methods for Producing Same, And Drugs", which was published on 21 Nov. 2013 with International Publication Number WO 2013/172732 A1, and which claims priority from Russian Patent Application No.: 2012120329 filed 16 May 2012, the content of which is incorporated herein by reference.

TECHNICAL FIELD

The invention relates to medicine and pharmacology, namely to the design of therapeutic drugs that are intended for the prevention and/or treatment of diverse viral diseases, in particular those caused by herpes viruses, and that are suitable for use in combination anticancer therapy and immunotherapy.

The invention relates to new germanium complex compounds with purine nitrogenous base derivatives (nucleoside analogues), hydroxycarboxylic acids, and preferably amino acids. In particular, the invention relates to germanium complex compounds with adenine and/or guanine derivatives, the preferred species being acyclovir, valacyclovir, gancyclovir, pencyclovir, vidarabine, and some others.

The claimed compounds provide a high level of biological, in particular antiviral, activity against herpes viruses, for example against herpes simplex virus type 1 and type 2, including resistant strains, for example, acyclovir-resistant strains.

THE BACKGROUND ART

Currently, some derivatives of nitrogenous bases are used as therapeutic drugs for the treatment and prevention of various viral infections, in particular infections caused by herpes virus, including the combination therapy of HIV-infected and cancer patients, and of patients with organ transplants. For example, guanine derivatives are used as antiviral therapeutic drugs, in particular for the treatment of infections caused by herpes virus.

Herpes is the most common human disease, the causative agent of which is herpes virus. There are known eight types of herpes viruses, the best known being herpes simplex viruses type 1 and type 2 (HSV-1 and HSV-2), Varicella-Zoster virus (HHV-3), Epstein-Barr virus (HHV-4), cytomegalovirus (HHV-5), and some others. Considerable part of population in the world is infected with herpes viruses in the form of latent infection. The herpes virus permanently exists in the nerve cells of the infected person, but the disease manifests itself clinically only during the exacerbation period, i.e. the period of active reproduction of the pathogen. HSV-1 is the cause of diseases such as keratitis, "cold on the lips," and encephalitis; HSV-2 causes genital infection; HHV-3 causes Varicella Zoster and shingles diseases; HHV-4 is the cause of infectious mononucleosis; and HHV-5 is the cause of cytomegaloviral hepatitis, colitis, and pneumonitis.

The therapeutic drugs used in order to treat diseases caused by herpes viruses are those capable of effectively suppressing the symptoms of virus infection, virus reproduction and development if received regularly. One such widely used therapeutic drug is acyclovir, which is a derivative of guanine and which inhibits the reproduction of the virus in cells. However, acyclovir is efficient in inhibiting virus reproduction when used in high doses; in particular the amount of this therapeutic drug for ingestion is up to 4,000 mg/day. Increasing one-time acyclovir dose reduces its bioavailability, and this can give rise to medicamental toxic effects on the body. One more disadvantage of acyclovir consists in its low water solubility: 1.3 mg/mL at 25° C. and 2.5 mg/mL at 37° C.; and moreover acyclovir is almost insoluble in hydrophobic systems. For this reason, acyclovir ingestion gives rise to some probability that fine crystals would form in the urea (see Mason, W. J., and Nickols H. H., "Crystalluria from acyclovir use," N. Engl. J. Med., 2008, 358: e14) and that nefrotoxicity would appear. In addition, acyclovir-resistant herpes virus strains have recently appeared with ever increasing frequency, especially in immunocompromised people.

Valacyclovir is a modified species of acyclovir and has higher activity and bioavailability: 54% against 15-20% for acyclovir. Nonetheless, valacyclovir, as acyclovir, is efficient only in high doses of 1,000 to 4,000 mg/day.

Other guanine derivatives, for example pencyclovir and gancyclovir, are also known to have activity against herpes simplex virus types 1 and 2 (HSV-1 and HSV-2), Varicella-Zoster virus, Epstein-Barr virus, and cytomegaloviral infections and to be useful for the treatment and prevention of infections caused by these viruses, in particular for the treatment and prophylaxis of immunocompromised persons, for example AIDS patients, cancer patients, and those with organ transplants. One common drawback of pencyclovir and gancyclovir consists in their moderate water solubilities (0.17% for pencyclovir and 0.43% for gancyclovir) and low bioavailabilities (1.5% and 5%, respectively).

Antiviral therapeutic drugs shall have the following properties: the ability to penetrate a cell, minimal cytotoxicity, selectivity, non-addictivity, and non-accumulation in the body. Therefore, one line in dosage form design consists in searching for compounds that would improve the antiviral activity of prior-art therapeutic drugs when formulated therewith. The patent EP 0477871 (1992, IPC: A61K 31/52) discloses an antiviral composition having selective and synergistic activity against herpes simplex virus types 1 and 2. That antiviral composition consists of at least two compounds which are derivatives of guanine: oxetanocin G (OXT-G), acyclovir (ACV), and carbocyclic oxetanocin G (C-OXT-G).

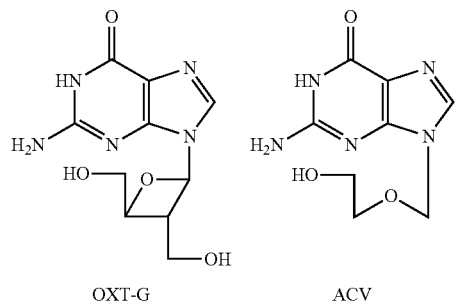

OXT-G          ACV

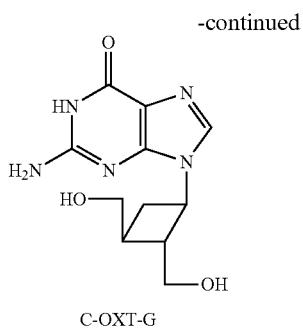

C-OXT-G

The effect of those antiviral compositions on the reproduction of herpes simplex virus types 1 and 2 (HSV-1 and HSV-2) was studied in Vero cell cultures. Monolayer Vero cell cultures were grown in Eagle's nutrient medium supplemented with 10% calf serum at a temperature of 37° C. Afterwards, the cultures were infected with HSV-1 and HSV-2. Then, guanine derivatives were inserted into the culture medium of infected cells either individually or in combinations with each other, and the concentrations that provided the 50% inhibition of the virus-induced cytopathic effect ($ID_{50}$) were determined. The compositions consisting of two compounds were shown to reach the $ID_{50}$ values at lower concentrations than those required for each of the individual components. For example, the combination of acyclovir (0.04-0.4 mcg/mL) with oxetanocin G (0.4-5.4 mcg/mL) or with carbocyclic oxetanocin G (0.01-0.2 mcg/mL) provides a synergistic effect against HSV-1, and the combination of acyclovir (0.1-3.4 mcg/mL) with oxetanocin G (0.4-4 mcg/mL) or with carbocyclic oxetanocin G (0.04-0.54 mcg/mL) provides a synergistic effect against HSV-2.

The Russian Federation patent 2240792 (2004, IPC: A61K 31/40) claims compositions comprising netropsin or a bis-derivative thereof with acyclovir and gancyclovir, these compositions providing high antiviral activity levels against herpes simplex viruses type 1 (HSV-1).

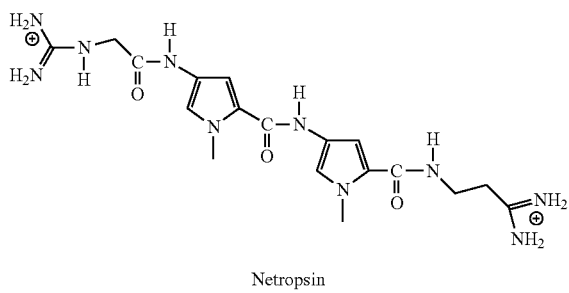 [SMILES: Cn1cc(NC(=O)c2cc(NC(=O)CNC(=N)[NH3+])cn2C)cc1C(=O)NCCC(N)=[NH2+]]

Netropsin

Combinations of netropsin compounds with acyclovir and gancyclovir provide an appreciable enhancement of the antiherpetic activity compared to each of the combined antiviral agents taken individually. For example, for the combined used of netropsin (2.5 mcg/mL) and bis-netropsin (0.15 mcg/mL) with acyclovir, the 50% inhibition of the virus-induced cytopathic effect is achieved for acyclovir concentrations of 0.075 mcg/mL and 0.15 mcg/mL, which is, respectively, five and three times lower than the concentration of acyclovir used alone (0.4 mcg/mL). A combination of netropsin and bis-netropsin with gancyclovir provides a fivefold reduction in gancyclovir concentration.

The U.S. Pat. No. 6448227 (2002, IPC: A61K 38/00) discloses a mixture containing S-acetyl glutathione and acyclovir as an agent against a herpes simplex virus or Varicella-Zoster virus. Glutathione is a tripeptide γ-glutamyl cysteinyl glycine.

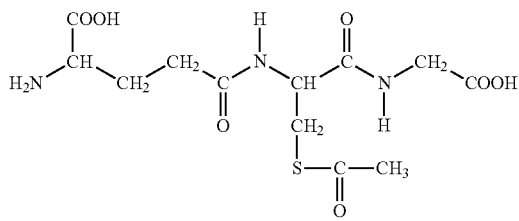 [SMILES: CC(=O)SCC(NC(=O)CCC(N)C(=O)O)C(=O)NCC(=O)O]

S-acetyl glutathione was shown to be an efficient agent against a herpes simplex virus (HSV-1) starting with concentrations of 0.35 mg/mL; acyclovir is especially efficient in concentrations of 0.45 mcg/mL. The combination of S-acetyl glutathione and acyclovir gives rise to a strong synergistic effect against HSV-1. For example, when S-acetyl glutathione (0.7 mg/mL) is used with acyclovir (0.45 mcg/mL), the virus titer is not determined.

Compositions of S-acetyl glutathione (0.35 mg/mL) with three acyclovir concentrations were shown to cause a noticeable synergistic effect against Varicella-Zoster virus, which was especially strong when the acyclovir concentration was 0.9 mcg/mL.

The Russian Federation patent 2104032 (1998, IPC: A61K 47/22) discloses a method for enhancing the efficiency of therapeutic drugs by means of organogermanium compounds (derivatives of germatrane). Organogermanium compounds were shown to enhance the activity of many known antiviral therapeutic drugs, such as adamantane derivatives (methadone and rimantadine), nucleoside analogues (acyclovir, gancyclovir, vidarabine, and idoxuridine), thiosemicarbazone derivatives (methisazone), and foscarnet. The therapeutic index increases fourfold with the simultaneous reduction of toxicity and alleviation of side effects. The antiviral activity of compositions consisting of germatrane derivatives with foscarnet or acyclovir was assayed in male guinea pigs infected with Herpes simplex virus HSV-2. Clinical studies showed that the use of germatrane derivatives formulated with foscarnet or acyclovir provided a twofold to fourfold enhancement in the effect of the latter in the treatment of HSV-2.

The German Patent 10343365 (2005, IPC: A61K 45/00) claims pharmaceutical compositions of xanthogenates (dithiocarbonates) in combination with antiviral therapeutic drugs for the treatment of viral diseases. Xanthogenates, especially tricyclodecan-9-yl-xanthogenate (D609), are well known for their antiviral and antitumor activity.

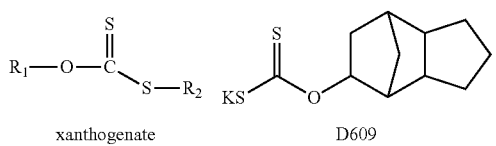

xanthogenate      D609

The use of xanthogenates as antiviral therapeutic drugs is complicated by the fact that high concentrations of these agents are required for treating living bodies. The last-cited patent demonstrates that the use of xanthogenate derivatives, such as D609, in combination with acyclovir results in an enhancement of antiviral activity. In the presence of low, inefficient concentrations of xanthogenate, the activity of acyclovir in a cell culture increased fivefold. In experiments on living bodies, the combination of D609 and acyclovir provided the survival of all animals infected with HSV-1.

It follows that the way used in the prior art for improving the antiviral activity of known therapeutic drugs involved the preparation of antiviral compositions comprising several active compound that enhanced the antiviral effect of the therapeutic drug.

The authors of this invention propose a radically different approach to improve the antiviral activity of known compounds. What is claimed according to the invention is: germanium complex compounds with derivatives of purine nitrogenous bases, hydroxycarboxylic acids, and amino acids, wherein these germanium complex compounds are individual chemical compounds having improved biopharmaceutical values, in particular high water solubilities, compared to the relevant purine nitrogenous base derivatives, and having higher antiviral activities than the relevant purine nitrogenous base derivatives.

OBJECTS OF THE INVENTION

One object of the present invention consists in providing new germanium complex compounds with purine nitrogenous base derivatives (nucleoside analogues), hydroxycarboxylic acids, and optionally but preferably amino acids, such that would have an antiviral activity, in particular against herpes viruses.

Another object of the invention consists in providing new germanium complex compounds with purine nitrogenous base derivatives (nucleoside analogues), hydroxycarboxylic acids, and optionally but preferably amino acids, such that would have an antiviral activity, in particular against herpes viruses, higher than the antiviral activities of the relevant nitrogenous bases.

Still another object of the invention consists in providing new germanium complex compounds with purine nitrogenous base derivatives (nucleoside analogues), hydroxycarboxylic acids, and optionally but preferably amino acids, such that would have good water solubilities.

One more object of the invention consists in providing a simple method for preparing new germanium complex compounds with various purine nitrogenous base derivatives (nucleoside analogues), hydroxycarboxylic acids of various natures, and amino acids of various natures, such that would be stable in solid state and could easily be transferred into aqueous solution.

Another object of the invention consists in developing a method for preparing germanium complex compounds with purine nitrogenous base derivatives (nucleoside analogues), hydroxycarboxylic acids, and optionally but preferably amino acids, such that would allow controlling the ratio between germanium, the purine nitrogenous base derivative, the hydroxycarboxylic acid, and the amino acid in the complex compound, that is, would allow controlling the composition of the complex compound.

One more object of the invention consists in providing an antiviral therapeutic drug comprising, as an active component, a germanium complex compound with purine nitrogenous base derivatives (nucleoside analogues), hydroxycarboxylic acids, and optionally but preferably amino acids.

A further object of the invention consists in using germanium complex compounds with purine nitrogenous base derivatives (nucleoside analogues), hydroxycarboxylic acids, and optionally but preferably amino acids, to manufacture a therapeutic drug for improving immunity.

Still further object of the invention consists in using germanium complex compounds with purine nitrogenous base derivatives (nucleoside analogues), hydroxycarboxylic acids, and optionally but preferably amino acids, for the treatment of and/or prevention of viral diseases, in particular those caused by a herpes virus.

BRIEF DISCLOSURE OF THE INVENTION

The claimed objects are achievable due to the provision of new organogermanium complex compounds comprising purine nitrogenous base derivatives (nucleoside analogues), whose compositions are described by the following structural formula:

$$Ge_x[AD][CA]_y[AA]_z \qquad (I)$$

wherein AD is a purine nitrogenous base derivative having an antiviral activity;
CA is a hydroxycarboxylic acid;
AA is an amino acid that can be selected from α-amino acids,
wherein x=1-2, y=2-4, and z=0-2, and wherein
all ADs in the complex compound are the same or different,
all CAs in the complex compound are the same or different, and
all AAs in the complex compound are the same or different.

Useful purine nitrogenous base derivatives (nucleoside analogues) in the context of the invention are adenine and/or guanine derivatives, preferably acyclovir, valacyclovir, ganciclovir, pencyclovir, and vidarabine.

The preferred hydroxycarboxylic acids to be used in the invention are citric acid, lactic acid, and/or malic acid.

The preferred amino acids to be used in the invention are arginine, glycine, lysine, and threonine.

Germanium complex compounds of structural formula (I) are individual chemical compounds that are well soluble in water and can be isolated in a solid form.

The germanium complex compounds of structural formula (I), comprising purine nitrogenous base derivatives, have high antiviral and immunostimulatory activity.

The method for preparing germanium complex compounds of structural formula (I) comprises: mixing germanium dioxide with water to provide an aqueous slurry of germanium dioxide; adding the resulting slurry with a mixture of a hydroxycarboxylic acid, a purine nitrogenous base derivative, and optionally, but preferably, an amino acid; heating the thus-obtained mixture at a temperature of 40-100° C. for 3-14 hours to form a desired product; and removing water by any known process to obtain a powdery product.

In the method of the invention, the aqueous slurry of germanium dioxide can be added with a mixture of more than one chemically different amino acids, and/or a mixture of more than one chemically different hydroxycarboxylic acids, and/or a mixture of different purine nitrogenous base derivatives.

DETAILS OF THE INVENTION

We have prepared new organogermanium complex compounds comprising purine nitrogenous base derivatives (nucleoside analogues), whose compositions are described by the following structural formula:

$$Ge_x[AD][CA]_y[AA]_z \qquad (I)$$

wherein AD is a purine nitrogenous base derivative having an antiviral activity;

CA is a hydroxycarboxylic acid;
AA is an amino acid selected from α-amino acids,
wherein x=1-2, y=2-4, and z=0-2, and wherein
all ADs in the complex compound are the same or different,
CAs in the complex compound are the same or different, and
all AAs in the complex compound are the same or different.

In the structural formula (I); x can have values of 1 or 2; y can be 2, 3, or 4; and z can be 0, 1, or 2; that is, each of x, y, and z is an integer.

Useful purine nitrogenous base derivatives (ADs) in the context of the invention are adenine and/or guanine derivatives that have antiviral activity, in particular against herpes viruses. Such derivatives are well known in the prior art. They are exemplified by guanine derivatives that belong to the cyclovir family, such as acyclovir (9-[(2-hydroxyethoxy) methyl] guanine), valacyclovir (2-(guanin-9-ylmethoxy) ethyl L-valine ether), gancyclovir (9-[(1,3-dihydroxy-2-propoxy)methyl]guanine), pencyclovir (9-[4-hydroxy-3-(hydroxymethyl) butyl]guanine), and others. Known adenine derivatives, for example, vidarabine (9-β-D-arabinofuranosyl adenine), are also useful in the context of the invention. In the art these compounds are alternatively referred to as nucleoside analogues. In the context of this application, these terms are interchangeable.

Preferred purine nitrogenous base derivatives (ADs) to be used in the invention are guanine derivatives that have antiviral activity, in particular against herpes viruses.

Useful hydroxycarboxylic acids (CAs) in the context of the invention are various hydroxycarboxylic acids, such as citric acid, lactic acid, malic acid, and other. Citric acid is preferred to be used in the method of the invention.

Useful amino acids (AAs) in the context of the invention are any α-amino acid, preferred being arginine, glycine, lysine, and threonine, and most preferred being arginine and lysine.

The compounds of structural formula (I) are individual chemical compounds which can be isolated in solid state as amorphous powders.

The individual chemical compounds of formula (I) are organogermanium compounds, comprising in one molecule more than one biologically active components, such as germanium and a nitrogenous base derivative that has antiviral activity. This endows the claimed compounds with a high antiviral and immunostimulatory activity. The hydroxycarboxylic acid and amino acid involved in the complex compound endow it with high water solubility. In addition, the amino acids and hydroxycarboxylic acids enhance the biological activity of the complex compounds of formula (I).

The invention provides a simple method, comprising a minimal number of steps, for preparing compounds of formula (I).

The method of the invention is characterized in that germanium dioxide is mixed with water to provide an aqueous slurry. To the stirred aqueous slurry of germanium dioxide, added are a nitrogenous base derivative, a hydroxycarboxylic acid, and an amino acid or a nitrogenous base derivative and a hydroxycarboxylic acid. More than one nitrogenous base derivatives, more than one hydroxycarboxylic acids, and more than one amino acids can be added according to the method. The mixture is stirred at 40-100° C. for 3-14 hours to obtain a solution of a desired product; then water is removed by any known process to obtain the desired product as a white amorphous powder.

The germanium dioxide used can be either α-germanium dioxide, which is insoluble in water, or β-germanium dioxide, which is water soluble. Water insoluble α-germanium dioxide is preferred because, when mixed with water, it forms an aqueous slurry of germanium dioxide.

Useful purine nitrogenous base derivatives (ADs) are adenine or guanine derivatives, which have antiviral activity, in particular against herpes viruses. The preferred derivatives to be used in the method are guanine derivatives of the cyclovir family, such as acyclovir (9-[(2-hydroxyethoxy) methyl] guanine), valacyclovir (2-(guanine -9-ylmethoxy) ethyl L-valine ether), gancyclovir (9-[(1,3-dihydroxy-2-propoxy) methyl]guanine), and pencyclovir (9-[4-hydroxy-3-(hydroxymethyl) butyl]guanine). Another embodiment of the method of the invention uses known adenine derivatives, for example, vidarabine (9-β-D-arabinofuranosyl adenine).

Useful hydroxycarboxylic acids (CAs) in the method of the invention are hydroxycarboxylic acids such as citric acid, lactic acid, malic acid, and other acids. Citric acid is preferred to be used in the method of the invention.

Useful amino acids (AAs) in the method of the invention are any α-amino acid, preferred being arginine, glycine, lysine, and threonine and most preferred being arginine and lysine.

The ratio between germanium, the purine nitrogenous base derivative, the hydroxycarboxylic acid, and the amino acid in the germanium complex compound depends on the amounts of the components added to the aqueous slurry of germanium dioxide. Regulating the proportions between the amounts of germanium dioxide and the amounts of the purine nitrogenous base derivative, hydroxycarboxylic acid, and amino acid, one can obtain complex compounds with different ratios between germanium, the purine nitrogenous base derivative, the hydroxycarboxylic acid, and the amino acid. When a nitrogenous base derivative is added to an aqueous solution of germanium dioxide in the stoichiometric proportion, the molar ratio between the nitrogenous base derivative and germanium dioxide in the resulting complex compound is 1:1. Regulating the molar ratio between the guanine derivative and germanium dioxide, one can thereby regulate the ratio between germanium and the purine nitrogenous base derivative in the resulting complex compound.

The ratio of germanium to the hydroxycarboxylic acid and the amino acid in the complex compound can be regulated in the same way. When a hydroxycarboxylic acid (or an amino acid) is added to an aqueous solution with germanium dioxide in the stoichiometric proportion, the molar ratio of germanium to the hydroxycarboxylic acid (or amino acid) in the resulting complex compound is 1:1. When the hydroxycarboxylic acid (or amino acid) is added in a doubled amount relative to the stoichiometry, the molar ratio of the hydroxycarboxylic acid (or amino acid) to germanium in the resulting complex compound is 2:1.

In a more detailed way the feasibility to prepare germanium complex compounds with various ratios between germanium, purine nitrogenous base derivatives, hydroxycarboxylic acids, and amino acids according to the invention is demonstrated by exemplary embodiments of the invention.

Regulating the composition of the germanium complex compound according to the invention allows one to obtain complex compounds containing various amounts of a purine nitrogenous base derivative. This constitutes an important advantage of the claimed complex compounds in the use as therapeutic drugs in the treatment of viral diseases, because of allowing the manufacture of therapeutic drugs having an increased or reduced antiviral activity.

The temperature at which the reaction is carried out to prepare germanium complex compounds with purine nitrogenous base derivative, hydroxycarboxylic acids, and optionally, but preferably, amino acids is in the range of 40-100°

C. Preferred temperatures are in the range of 80-100° C.; more preferred temperatures are in the range of 85-100° C.

Reaction times are in the range of 3-14 hours. Preferred reaction times are in the range of 5-12 hours; more preferred reaction times are in the range of 6-8 hours.

The formation of an organogermanium complex is monitored by the complete dissolution of germanium dioxide (when the insoluble germanium dioxide is used) and the formation of a clear solution. Any other methods are also useful for monitoring the product formation, for example, those involving sampling and analyzing the samples.

In order to isolate an organogermanium complex compound, the solution is filtered and then water is removed from the solution by any known process. Any of the known processes is suitable for this purpose, for example, water evaporation, vacuum distillation under heating, or lyophilic drying (freeze drying). The desired compounds are obtained as amorphous powders.

Purine nitrogenous base derivatives, hydroxycarboxylic acids, and amino acids can be added to an aqueous slurry of germanium dioxide either simultaneously, or by consecutively introducing these components. The order in which the components are added does not substantially affect the resulting desired product, which is a germanium complex with purine nitrogenous base derivatives, hydroxycarboxylic acids, and amino acids, if such are added.

One embodiment of the method is a method comprising: adding a hydroxycarboxylic acid to an aqueous slurry of germanium dioxide and heating the thus-obtained mixture under stirring at 80-100° C. for 6-10 hours until a clear solution is formed; then adding an amino acid and a purine nitrogenous base derivative, in particular a guanine derivative; and continuing heating at 80-100° C. for 2-3 hours, filtering the solution, and removing water to obtain a complex compound.

Another embodiment of the method is a method comprising: adding an amino acid to an aqueous slurry of germanium dioxide; heating the thus-obtained mixture under stirring at 80-100° C. for 3-5 hours until a clear solution is formed; then adding a hydroxycarboxylic acid and a purine nitrogenous base derivative, in particular a guanine derivative; and continuing heating at 80-100° C. for 3-5 hours, filtering the solution, and removing water to obtain a complex compound in a solid form.

Still another embodiment of the method is a method comprising: adding an amino acid and a hydroxycarboxylic acid to an aqueous slurry of germanium dioxide; heating the thus-obtained mixture under stirring at 80-100° C. for 6-8 hours until a clear solution is formed; then adding a purine nitrogenous base derivative, in particular a guanine derivative; and continuing heating at 80-100° C. for 2-3 hours, filtering the solution, and removing water to obtain a complex compound in a solid form.

One more embodiment of the method is a method comprising: adding a mixture of an amino acid, a hydroxycarboxylic acid, and a purine nitrogenous base derivative, in particular a guanine derivative, to an aqueous slurry of germanium dioxide; heating the thus-obtained mixture under stirring at 80-100° C. for 6-12 hours until a clear solution is formed; filtering the solution; and removing water to obtain a complex compound in a solid form.

Still one more embodiment of the method is a method comprising: adding a hydroxycarboxylic acid to an aqueous slurry of germanium dioxide and heating the thus-obtained mixture under stirring at 80-100° C. for 8-9 hours until a clear solution is formed. This is followed by adding a purine nitrogenous base derivative, in particular a guanine derivative; continuing heating at 80-100° C. for 2-3 hours, filtering the solution, and removing water to obtain a complex compound in a solid form.

The product is obtained as a white amorphous powder, which is readily soluble in water. Noteworthy, most guanine derivatives are, as a rule, poorly soluble in water (except for valacyclovir). For example: the water solubility of acyclovir is 2.5 mg/mL at 37° C., the water solubility of gancyclovir is 4.3 mg/mL at 25° C., the water solubility of pencyclovir is 1.74 mg/mL at 20° C., and the water solubility of valacyclovir is 174 mg/mL at 25° C. In the same manner, adenine derivatives have limited water solubilities; for example, vidarabine is poorly soluble in water and is used as an ointment. The germanium complex compounds prepared according to the invention have good water solubilities exceeding 25 wt % at 20° C., i.e., exceeding 250 mg/mL at 20° C. The high solubilities of the germanium complex compounds prepared according to the invention allow aqueous solutions with high concentrations of these compounds to be prepared and used as antiviral therapeutic drugs without causing nefrotoxicity side effects.

NMR and IR spectra were studied for germanium complex compounds with purine nitrogenous base derivatives, in particular guanine derivatives, hydroxycarboxylic acids, and amino acids, if such were used, which were prepared according to the invention, and elemental analysis was also performed for these compounds. The results indicate that these germanium complex compounds have the general structural formula:

$$Ge_x[AD][CA]_y[AA]_z \qquad (I)$$

wherein AD is a purine nitrogenous base derivative having an antiviral activity; CA is a hydroxycarboxylic acid; AA is an α-amino acid, wherein x=1-2, y=2-4, and z=0-2, wherein each of x, y, and z is an integer, and wherein all ADs in the complex compound are the same or different, all CAs in the complex compound are the same or different, and all AAs in the complex compound are the same or different.

The presence of a purine nitrogenous base, an amino acid, and a hydroxycarboxylic acid endows germanium complex compounds with high biological activity and good water solubility, so that these compounds would be useful in the manufacture of new pharmaceutical compositions and therapeutic drugs for diverse medicinal applications. Altering the nature of a purine nitrogenous base, an amino acid, and/or a hydroxycarboxylic acid offers a way to prepare germanium complex compounds that would have a very high biological activity for use in manufacturing highly efficient pharmaceuticals. We propose using the germanium complex compounds according to the present invention as the active component in these pharmaceuticals and therapeutic drugs. The preferred germanium complex compounds as claimed are expected to have the same type of biological activity as the involved purine nitrogenous bases have, just as will be demonstrated below for the compounds prepared according to Examples 1 and 5. A germanium complex compound, however, can also have another type of biological activity such that is not intrinsic to the initial components involved therein. Germanium complex compounds are intended for use in effective amounts. Pharmaceutical compositions and formulations may in addition contain conventional auxiliary components, which are well known in the prior art.

Below we describe exemplary preparations of germanium complex compounds with purine nitrogenous base derivatives, in particular guanine and adenine derivatives, hydroxycarboxylic acids, and amino acids, if such are used.

These examples serve exclusively to illustrate the method for preparing germanium complex compounds, and in no means are intended to limit the invention to these examples.

EXAMPLE 1

To a round-bottomed flask equipped with a stirrer and a thermometer, charged are 3.12 g (0.03 mol) α-germanium dioxide and 12.6 g (0.06 mol) citric acid monohydrate, and 200 mL distilled water. The slurry is stirred under heating (at 85-95° C.) for 8-9 hours until a clear solution is formed. Then, added are 2.61 g (0.015 mol) arginine and 3.38 g (0.015 mol) acyclovir, and stirring under heating (at 85-95° C.) is carried out for 2 hours. Following this, the solution is cooled and filtered, and water is removed on a rotary evaporator. The product is obtained as 19.5 g (95%) of a white amorphous powder.

Figure 2:
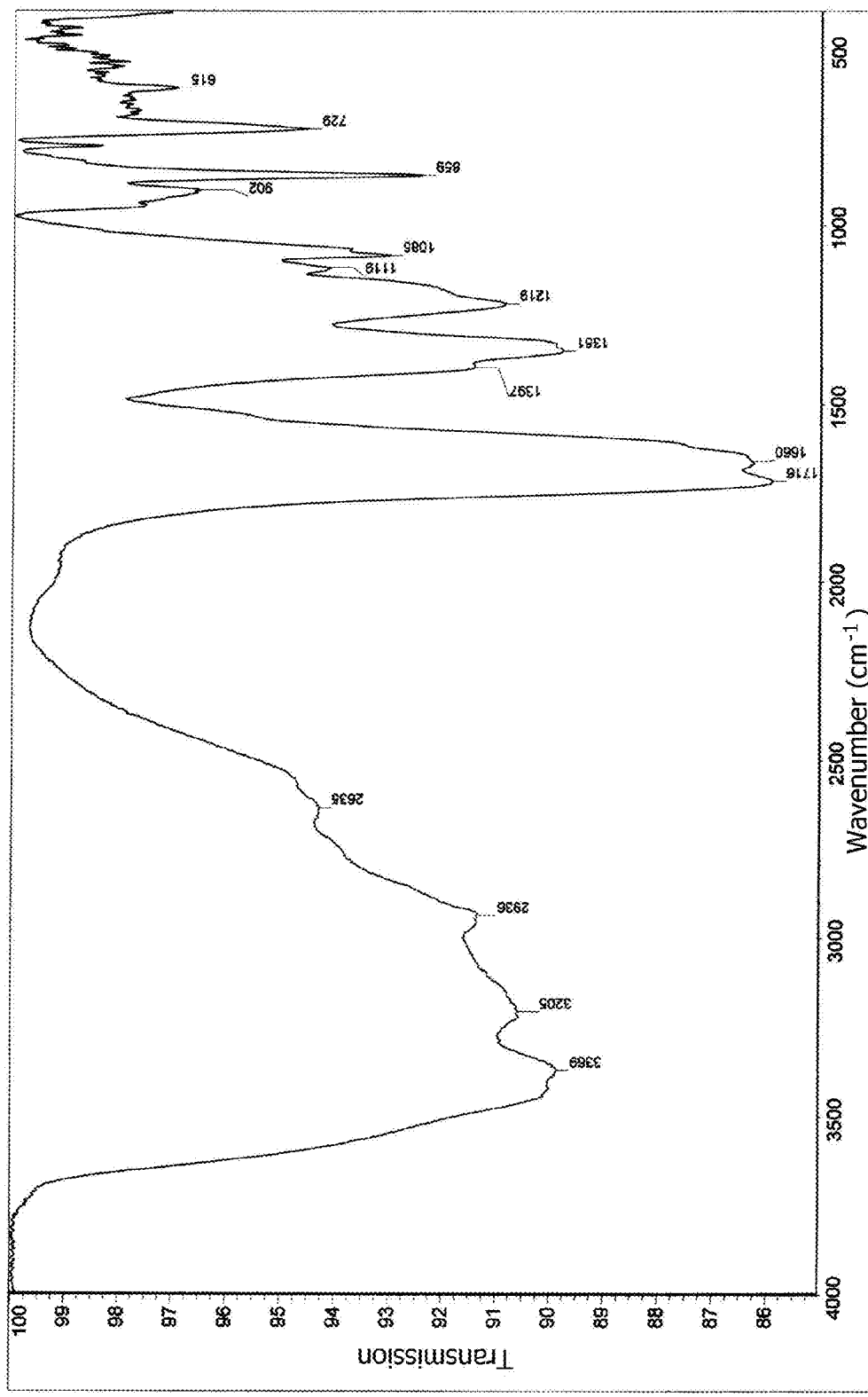

NMR and IR spectra were measured and interpreted, and elemental analysis data were obtained for the germanium complex compound prepared according to Example 1. FIG. 1 displays a $^1$H NMR spectrum in $D_2O$ for the germanium complex compound with arginine, citric acid, and acyclovir. FIG. 2 displays an IR spectrum of the germanium complex compound with arginine, citric acid, and acyclovir. Elemental analysis data for the compound prepared according to Example 1 are displayed in Table 1. The compound prepared according to Example 1 is hereinafter denoted as WDS-1.

EXAMPLE 2

To a round-bottomed flask equipped with a stirrer and a thermometer, charged are 3.12 g (0.03 mol) α-germanium dioxide, 12.6 g (0.06 mol) citric acid monohydrate, 4.5 g (0.06 mol) glycine, 9.73 g (0.03 mol) valacyclovir, and 250 mL distilled water. The slurry is stirred under heating (at 85-95° C.) for 10-12 hours. The resulting clear solution is cooled and filtered, and water is removed on a rotary evaporator. The product is obtained as 27.1 g (94%) of a white amorphous powder. Relevant elemental analysis data are displayed in Table 1. The compound of this example is hereinafter denoted as WDS-2.

EXAMPLE 3

To a round-bottomed flask equipped with a stirrer and a thermometer, charged are 3.12 g (0.03 mol) α-germanium dioxide, 12.6 g (0.06 mol) citric acid monohydrate, 7.6 g (0.03 mol) pencyclovir, and 250 mL distilled water. The slurry is stirred under heating (at 85-95° C.) for 7-9 hours until a clear solution is formed. Then added are 5.22 g (0.03 mol) arginine, and stirring under heating (at 85-95° C.) is carried out for 2 hours. Following this, the solution is cooled and filtered, and water is removed on a rotary evaporator. The product is obtained as 26 g (95%) of a white amorphous powder. Relevant elemental analysis data are displayed in Table 1. The compound of this example is hereinafter denoted as WDS-3.

EXAMPLE 4

To a round-bottomed flask equipped with a stirrer and a thermometer, charged are 3.12 g (0.03 mol) α-germanium dioxide, 7.14 g (0.06 mol) threonine, and 250 mL distilled water. The slurry is stirred under heating (at 85-95° C.) for 5-7 hours. Then added are 7.65 g (0.03 mol) gancyclovir and 8.04 g (0.06 mol) malic acid, and the mixture is stirred under heating (at 85-95° C.) for 3 hours. Following this, the solution is cooled and filtered, and water is removed on a rotary evaporator. The product is obtained as 23.1 g (93%) of a white amorphous powder. Relevant elemental analysis data are displayed in Table 1. The compound of this example is hereinafter denoted as WDS-4.

EXAMPLE 5

To a round-bottomed flask equipped with a stirrer and a thermometer, charged are 3.12 g (0.03 mol) α-germanium dioxide, 2.46 g (0.015 mol) lysine monohydrate, 12.6 g (0.06 mol) citric acid monohydrate, and 200 mL distilled water. The slurry is stirred under heating (at 85-95° C.) for 6-7 hours until a clear solution is formed. Then added are 3.38 g (0.015 mol) acyclovir, and stirring is carried out under heating (at 85-95° C.) for 2 hours. Following this, the solution is cooled and filtered, and water is removed on a rotary evaporator. The product is obtained as 19.2 g (94%) of a white amorphous powder.

Figure 3:
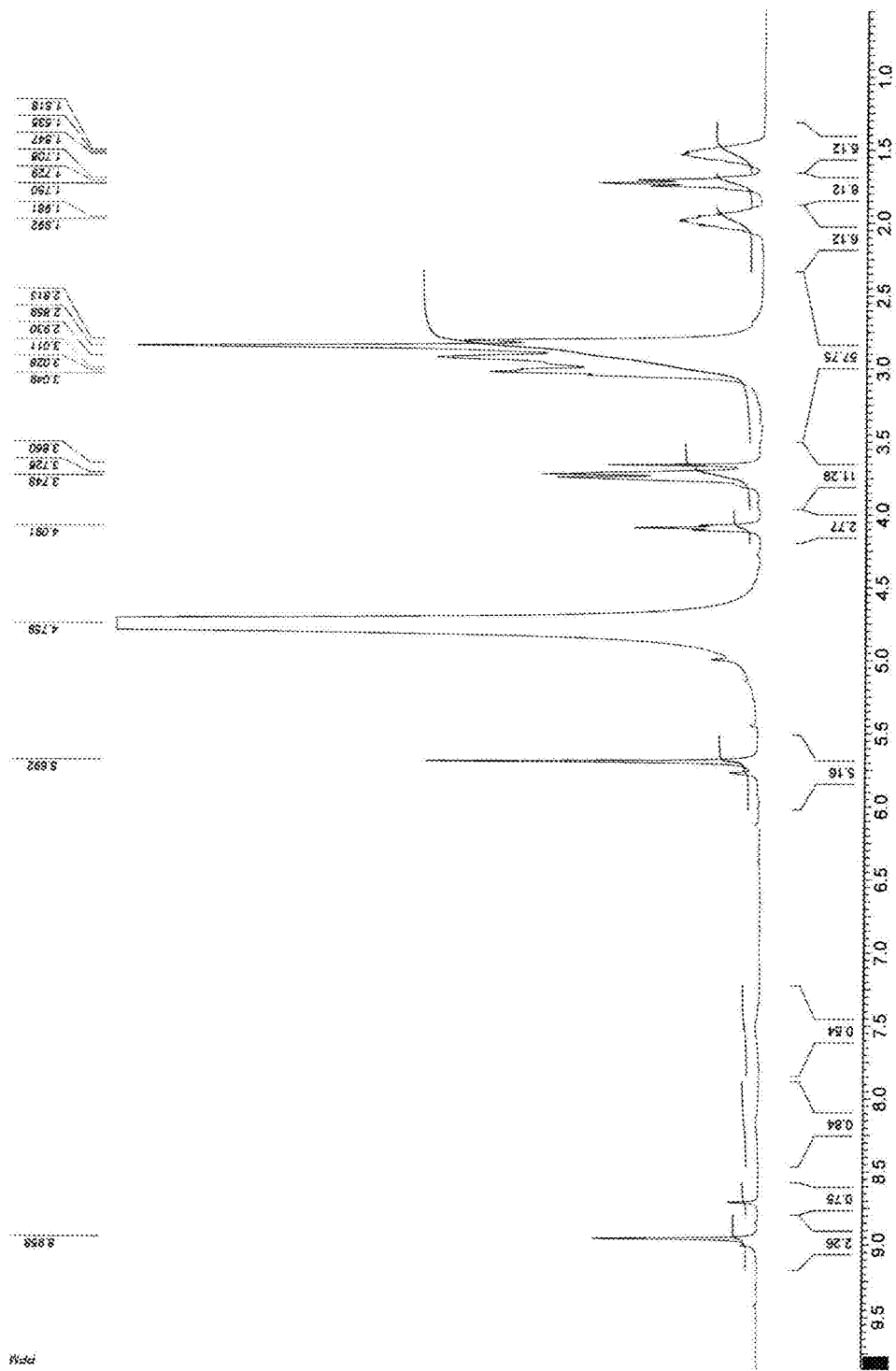
Figure 4:
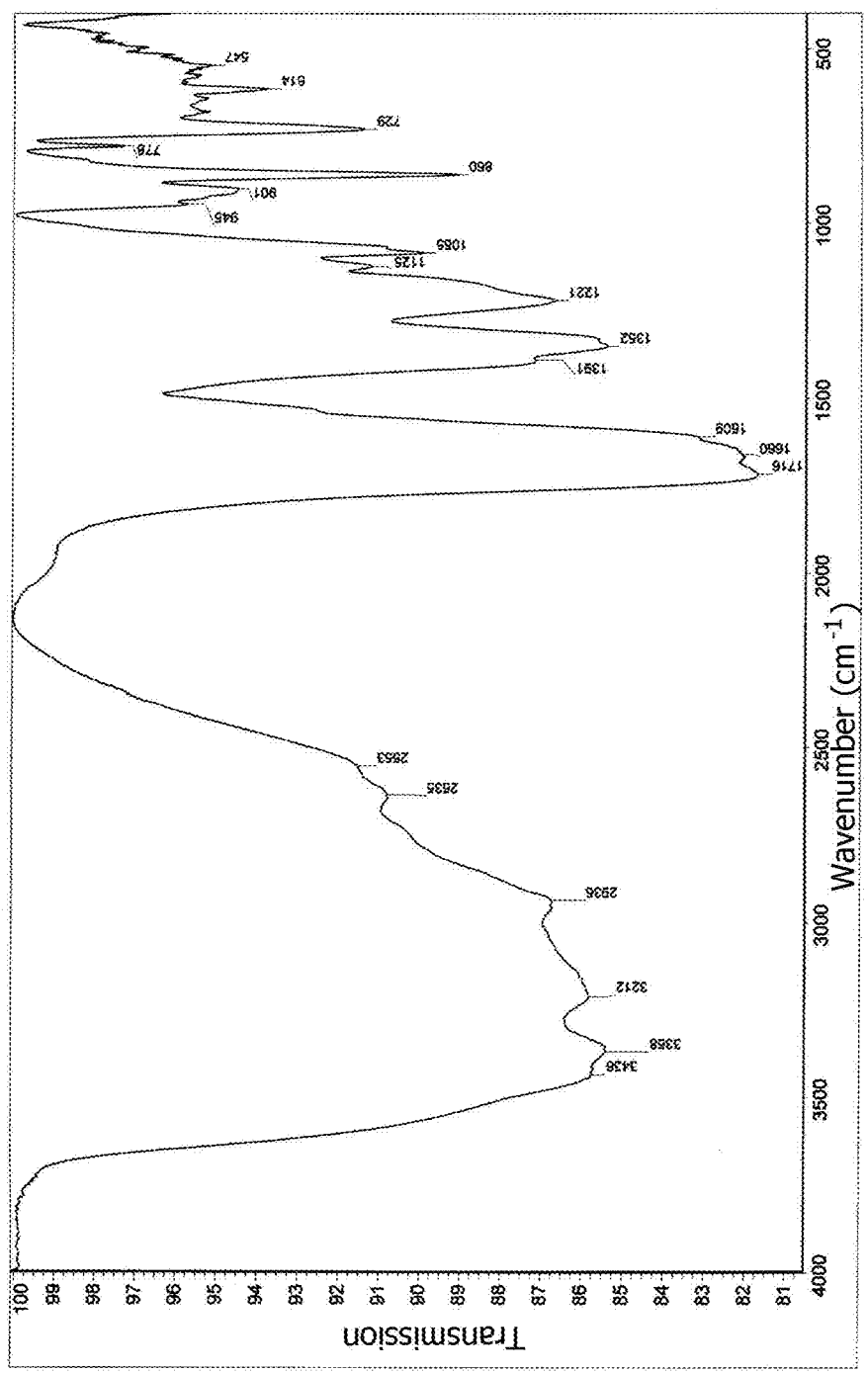

NMR and IR spectra for the compound prepared according to Example 5 are shown in FIG. 3 and FIG. 4, respectively. Relevant elemental analysis data are displayed in Table 1. The compound of this example is hereinafter denoted as WDS-5.

EXAMPLE 6

To a round-bottomed flask equipped with a stirrer and a thermometer, charged are 3.12 g (0.03 mol) α-germanium dioxide, 12.6 g (0.06 mol) citric acid monohydrate, and 200 mL distilled water. The slurry is stirred under heating (at 85-95° C.) for 8-9 hours until a clear solution is formed. Then added are 3.38 g (0.015 mol) acyclovir, and stirring is carried out under heating (at 85-95° C.) for 2 hours. Following this, the solution is cooled and filtered, and water is removed by freeze drying. The product is obtained as 16.9 g (94%) of a white amorphous powder. Relevant elemental analysis data are displayed in Table 1. The compound of this example is hereinafter denoted as WDS-6.

EXAMPLE 7

To a round-bottomed flask equipped with a stirrer and a thermometer, charged are 3.12 g (0.03 mol) α-germanium dioxide, 12.6 g (0.06 mol) citric acid monohydrate, and 200 mL distilled water. The slurry is stirred under heating (at 85-95° C.) for 8-9 hours until a clear solution is formed. Then added are 8.55 g (0.03 mol) vidarabine monohydrate, and stirring is carried out under heating (at 85-95° C.) for 2 hours. Following this, the solution is cooled and filtered, and water is removed by freeze drying. The product is obtained as 20.5 g (95%) of a white amorphous powder. Relevant elemental analysis data are displayed in Table 1. The compound of this example is hereinafter denoted as WDS-7.

TABLE 1

Elemental analysis data for the compositions prepared.

| Example no. | Compound | Formula | FW | Found, % | | | | Calcd., % | | | |
|---|---|---|---|---|---|---|---|---|---|---|---|
| | | | | C | H | Ge | N | C | H | Ge | N |
| 1 | WDS-1 | $Ge_2[Arg][Citr]_4[Acv]$ | 1305 | 34.62 | 3.91 | 11.32 | 9.45 | 34.97 | 3.78 | 11.13 | 9.66 |
| 2 | WDS-2 | $Ge[Gly]_2[Citr]_2[Vcv]$ | 927 | 37.34 | 4.73 | 7.98 | 11.86 | 37.56 | 4.56 | 7.83 | 12.08 |
| 3 | WDS-3 | $Ge[Arg][Citr]_2[Pcv]$ | 880 | 38.01 | 4.81 | 8.37 | 14.19 | 38.20 | 4.69 | 8.25 | 14.32 |
| 4 | WDS-4 | $Ge[Thr]_2[Mal]_2[Gcv]$ | 830 | 35.96 | 4.84 | 8.89 | 11.68 | 36.17 | 4.73 | 8.75 | 11.81 |
| 5 | WDS-5 | $Ge_2[Lys][Citr]_4[Acv]$ | 1277 | 35.56 | 3.98 | 11.49 | 7.53 | 35.74 | 3.87 | 11.37 | 7.68 |
| 6 | WDS-6 | $Ge_2[Citr]_4[Acv]$ | 1130 | 33.83 | 3.27 | 12.97 | 6.03 | 34.01 | 3.12 | 12.84 | 6.19 |
| 7 | WDS-7 | $Ge[Citr]_2[Vdrb]$ | 720 | 36.51 | 3.62 | 10.17 | 9.55 | 36.70 | 3.50 | 10.08 | 9.72 |

Arg stands for arginine, Gly stands for glycine, Lys for lysine, Thr for threonine, Citr stands for citric acid, Mal stands for malic acid, Acv stands for acyclovir, Vcv stands for valacyclovir, Gcv stands for gancyclovir, Pcv stands for pencyclovir, and Vdrb stands for vidarabine.

ACUTE TOXICITY

The acute toxicity of the new compounds, in particular of those prepared according to Examples 1, 5 and 6, was determined in nonlinear male white mice having body weights of 18-20 g with one-time intragastric (i/g) administration, at doses of 1,000, 2,000, 3,000, 4,000, and 5,000 mg/kg, of 20% aqueous solution in amounts of 0.1, 0.2, 0.3, 0.4, and 0.5 mL per 20 g mouse body weight, respectively. Each of the compounds was administered individually. Signs of intoxication, a lag in body weight gain, or death of animals was not observed in 14 days after each of the compounds was administered. No violations in the movements, reflexes, or behavior of animals were observed over the range of the doses studied. Anatomical studies have not discovered any change in the lungs, kidneys, spleen, or other organs. $LD_{50}$ values in mice for the compounds studied were greater than 5,000 mg/kg, and thereby these compounds can be classified as Class IV hazard in terms of the hazard classification of substances by their impact on the body according to the Russian State Standard (GOST) 12.1.007-76 or as Class V toxicity (practically nontoxic) according to the Hodge and Sterner scale (1943).

Experiments also discovered no skin-irritating, skin-resorptive, or sensitizing effect of the tested compounds.

The tested compounds are not accumulated in the body and have no cumulative properties. When the compounds were administered to nonlinear mice for 14 days intragastrically at a dose of 1,000 mg/kg, the animals of the experimental group showed no death and no changes in the body weight or the weight coefficients of parenchymatous organs (liver, kidneys, and spleen) compared to the respective values in control group animals.

BIOPHARMACEUTICAL VALUES

The solubility of a drug in biological fluids of the gastrointestinal tract (gastric fluid, intestinal fluid) is an important biopharmaceutical property. We have studied selected biopharmaceutical values for some of the newly prepared compounds, in particular for WDS-1 and WDS-5, compared to acyclovir. Tests were carried out subject to the requirements of the *Guidance on the Investigation of Bioequivalence,* European Medicines Agency (EMA), Committee for Medicinal Products of Human Use (CHMP), 2010.

For this purpose, we studied the solubilities of these compounds at various pH values that correspond to the gastrointestinal fluids (for the intestinal fluid: pH is 1.2; for the duodenal fluid: pH 4.4; and for the small intestine fluid: pH 6.8).

One biopharmaceutical solubility value which allows describing a therapeutic drug (TD) as a compound having "high" or "low" solubility, is the dose/solubility ratio (D/S). The dose/solubility ratio is determined as follows: maximal dose (D) (mg)/water solubility (S) (mg/mL). When D/S≤250 mL, the TD has "high" solubility in the relevant aqueous solution.

Importantly, biopharmaceutical solubility is not a constant value for a given therapeutic drug (TD); rather, it depends on the maximal registered dosage of an immediate-release TD intended for systemic effects. In these experiments the dose/solubility ratio was calculated using the maximal acyclovir dosage in the tablet dosage form registered for medicinal use in the Russian Federation (800 mg).

One more biopharmaceutical value is the solubility in biorelevant media. These are dissolution media such that approach the human body fluids (intestinal fluid and gastric fluid) as closely as possible in terms of chemical composition and in terms of physicochemical properties (pH, osmomolality, buffer capacity, and surface tension). The simulation of physiological conditions is provided by introducing surfactants (lecithin and sodium taurocholate) into these media. There are two major types of biorelevant media, namely: an artificial intestinal fluid in an empty stomach (fasted state simulated intestinal fluid (FaSSIF)) and after eating (fed state simulated intestinal fluid (FeSSIF)). Differences between the solubilities of a compound in these media may be taken into account in optimizing dosage regimens (to be taken with an empty stomach or after eating). When the maximal dosage of a therapeutic drug completely dissolves in a 250-mL portion of each of these media, we may treat this drug as having "high" biorelevant solubility.

A criterion that can serve as a measure of the absorption of the solute through the wall of the small intestine is permeability, i.e., the fraction of the substance permeating through the intestinal wall. The physicochemical property of a molecule that makes the greatest contribution to permeability is liphophilicity. A measure of lipophilicity to be used in indirect assessment of intestinal permeability is the octanol-water partition coefficient, log P, which is the logarithm of the ratio of concentrations of an unionized substance in the system of two immiscible liquids (n-octanol and water). An indirect criterion of "high" (exceeding 90%) intestinal permeability is the following: when the partition coefficient log P exceeds the value for a reference substance (metoprolol, for which log P=1.72), intestinal permeability is considered to be high. The results of experiments are compiled in Table 2.

TABLE 2

Biopharmaceutical values of compounds WDS-1 and WDS-5 as compared to acyclovir

| dissolution medium | acyclovir | WDS-1 | WDS-5 |
|---|---|---|---|
| Solubility, mg/mL | | | |
| pH 1.2 | 3.5 | >32 | >64 |
| pH 4.4-4.5* | 2.6 | >32 | >64 |
| pH 6.8 | 2.4 | >32 | >64 |
| FaSSIF | 1.44 | >32 | >64 |
| FeSSIF | 1.38 | >32 | >64 |
| Ratio D/S, mL | | | |
| pH 1.2 | <229 | <25 | <12.5 |
| pH 4.4-4.5* | 308 | <25 | <12.5 |
| pH 6.8 | 333 | <25 | <12.5 |
| FaSSIF | 555.5 | <25 | <12.5 |
| FeSSIF | 579.7 | <25 | <12.5 |
| Solubility ("high"/"low") | | | |
| pH 1.2 | "high" | "high" | "high" |
| pH 4.4-4.5* | "low" | "high" | "high" |
| pH 6.8 | "low" | "high" | "high" |
| FaSSIF | "low" | "high" | "high" |
| FeSSIF | "low" | "high" | "high" |
| Octanol-water partition coefficient | | | |
| Log P | -1.57 | -1.57 | -1.66 |

*pH is 4.4 for the tested compounds and 4.5 for acyclovir.

Thus, the biopharmaceutical solubilities of the germanium complex compounds prepared according to the invention may be considered to be "high" over the entire range of physiological pH values, corresponding to pH values in the stomach, duodenum, or the initial section of the small intestine. Noteworthy, the solubility values for the germanium complex compounds according to the invention differ from the solubility of acyclovir not only quantitatively, but also qualitatively. So, solubility values for the germanium complex compounds are at least 10 times the solubility of acyclovir, and moreover, the solubilities of the germanium complex compounds according to the invention are "high" over the entire pH range studied, whereas the solubility of acyclovir at pH 44-4.5 and 6.8 is "low".

The biorelevant solubilities of the germanium complex compounds according to the invention in both biorelevant media (FaSSIF and FeSSIF) are "high", and moreover more than 10 maximal dosages of the substance dissolve per 250 mL. Inasmuch as the solubilities in both biorelevant media are high, eating will not be a rate-limiting process for the dissolution of the substance in the gastrointestinal tract environment, and other factors should be taken into account in optimizing dosage regimens (for example, whether irritating is caused to the gastrointestinal wall, whether the compound is destroyed when eaten, etc.).

The partition coefficients log P for the studied germanium complex compounds according to the invention are lower than for metoprolol, and their values are commensurate to the partition coefficient log P for acyclovir. Thus, the intestinal permeabilities of these compounds may be characterized as "low". In view of the high biopharmaceutical solubilities of these compounds (which were discussed above and demonstrated in Table 2), the germanium complex compounds according to the invention are, at the same time, to be expected to have higher bioavailabilities than the bioavailability of acyclovir. However, it cannot be ruled out that absorption through the intestinal wall will be the rate-controlling stage for the compounds according to the invention to enter the bloodstream.

On the whole, having lipophilicities similar to that of acyclovir, the germanium complex compounds according to the invention have far higher biorelevant and biopharmaceutical solubilities, and this might serve as evidence of their higher bioavailabilities.

ANTIVIRAL ACTIVITY (A) In Vitro Antiviral Activity Studies of the Germanium Complex Compounds According to the Invention.

The antiviral activity of the new germanium compounds according to the invention, in particular WDS-1 and WDS-5, was studied in vitro on green monkey kidney cell (VERO) culture in accordance with conventional techniques (see Gus'kova, T. A., Nikolaeva, I. S., and Peters, V. V., "Methodological Guidance to Study Antiviral Activity of Pharmacological Agents" in "The Manual on the Experimental (Preclinical) Study of New Pharmacological Agents," Moscow, Ministry of Public Healthcare of the Russian Federation, Remedium IPA, CJSC, 2000, pp. 274-280;
Cotarelo, M., Catalan, P., Sanchez-Carrillo, C., Menasalvas, A., Cercenado, E., et al., "Cytopathic effect inhibition assay for determining the in vitro susceptibility of herpes simplex virus to antiviral agents," J. Antimicrob. Chemother., 1999, Vol. 44, pp. 705-708;
Kruppenbacher, J. P., Klass, R., and Eggers, H. J., "A rapid and reliable assay for testing acyclovir sensitivity of clinical herpes simplex virus isolates independent of virus dose and reading time," Antiviral Res., 1994, Vol. 23, pp. 11-22; and Flint, S. J., Enquist, W., Racaniello, V. R., and Skalka, A. M., (2009). "Virological Methods" in Principles of Virology, ASM Press).

The reference used was acyclovir and valacyclovir, respectively.

The test virus used to study antiviral activity was the herpes simplex virus type I (HSV) strain, which is highly resistant to acyclovir (strain "L2/R").

The criteria used to evaluate the antiviral activity were: the ability to prevent the development of a virus-induced cytopathic effect and the ability to inhibit reproduction of the virus in the cell culture. Test samples were inserted into the nutrient medium 1 hour after the culture was infected with a certain dose of the virus (the therapeutic scheme). The antiviral activity of the samples and virus-induced cytopathic effects in the cell culture were monitored every day using light microscopy as the degree of morphological alteration of a cell monolayer. The endpoint was on the 4th day of contact of the cells with the infectious material, after a well-defined (100%) cytopathic effect appeared in control samples (positive control). The presence of antiviral activity in samples of organogermanium compounds according to the invention was ascertained as the difference between the viral titers measured in the experiment and in the control. Viral titers were determined according to Reed and Muench (Reed, L. J. and Muench, H., "A simple method of estimating fifty percent endpoints," The American Journal of Hygiene 1938, 27: 493-497). When difference between the titers was ≤1.5 log $TCD_{50}$, the cytopathic tissue culture dose causing 50% cell death in a monolayer ($TCD_{50}$ is the tissue culture dose causing cytopathology in 50% of cultured cells), the compound was regarded as having a low antiviral activity; when the difference was in the range between 1.5 and 2.0 log $TCD_{50}$, the compound was regarded as having a moderate antiviral activity; and when the difference was ≥2.0 log $TCD_{50}$, the compound had a well-defined HSV-inhibitory activity.

In this experiment, an acyclovir sample in the range of concentrations from 500 to 100 mcg/mL significantly reduced the infectious activity of the virus by a value in the range from 2.0 log to 1.0 log. A valacyclovir sample in concentrations of 500 mcg/mL and 250 mcg/mL significantly reduced the infectious activity of the HSV-1 "L2/R" virus by 1.5 log. A sample of the complex compound WDS-1 according to the invention in the range of concentrations equivalent to 400 to 160 mcg/mL acyclovir significantly reduced the infectious activity of the HSV-1 "L2/R" virus by a value in the range of 3.25-1.5 log $TCD_{50}$. A sample of the complex compound WDS-5 according to the invention in the range of concentrations equivalent to 400 to 160 mcg/mL acyclovir significantly reduced the infectious activity of the HSV-1 "L2/R" virus by a value in the range of 1.75-1.0 log $TCD_{50}$.

(B) In Vivo Antiviral Activity Studies of Germanium Complex Compounds According to the Invention.

(a) Therapeutic Antiviral Activity of Compounds According to the Invention.

The in vivo experiment intended to assess the therapeutic efficiency of compound WDS-1 according to the invention, which was prepared using acyclovir, was carried out on induced herpetic ophthalmic herpes (keratitis) in rabbits (Kaufman, H. E., Martola, E. L., and Dohlman, C. H., "The use of 5-iodo-2-deoxyuridine (IDU) in the treatment of herpes simplex keratitis," Arch. Ophthalmol. 1962; 68:235-239). Animals were infected with a culture fluid containing HSV-1 at a dose of 10 $TCID_{50}$ ($TCID_{50}$ is the tissue culture 50% infectious dose, which causes 50% cell lesion of the monolayer), which was applied using a pipette to a pre-abraded corneas (followed by rubbing). The treatment of HSV-infected rabbits was started 48 hours post-infection. The agent was administered per os daily 6 times a day in a concentration of 10 mg/mL for 8 days.

The use of the compound WDS-1 according to the invention showed a well-defined positive therapeutic effect and resulted in a statistically significant alleviation of the severity of the clinical picture of ophthalmic herpes, a reduced disease duration, and prevented development of complications of the herpetic eye infection with meningoencephalitis, compared to the respective values in the control group.

Figure 5:
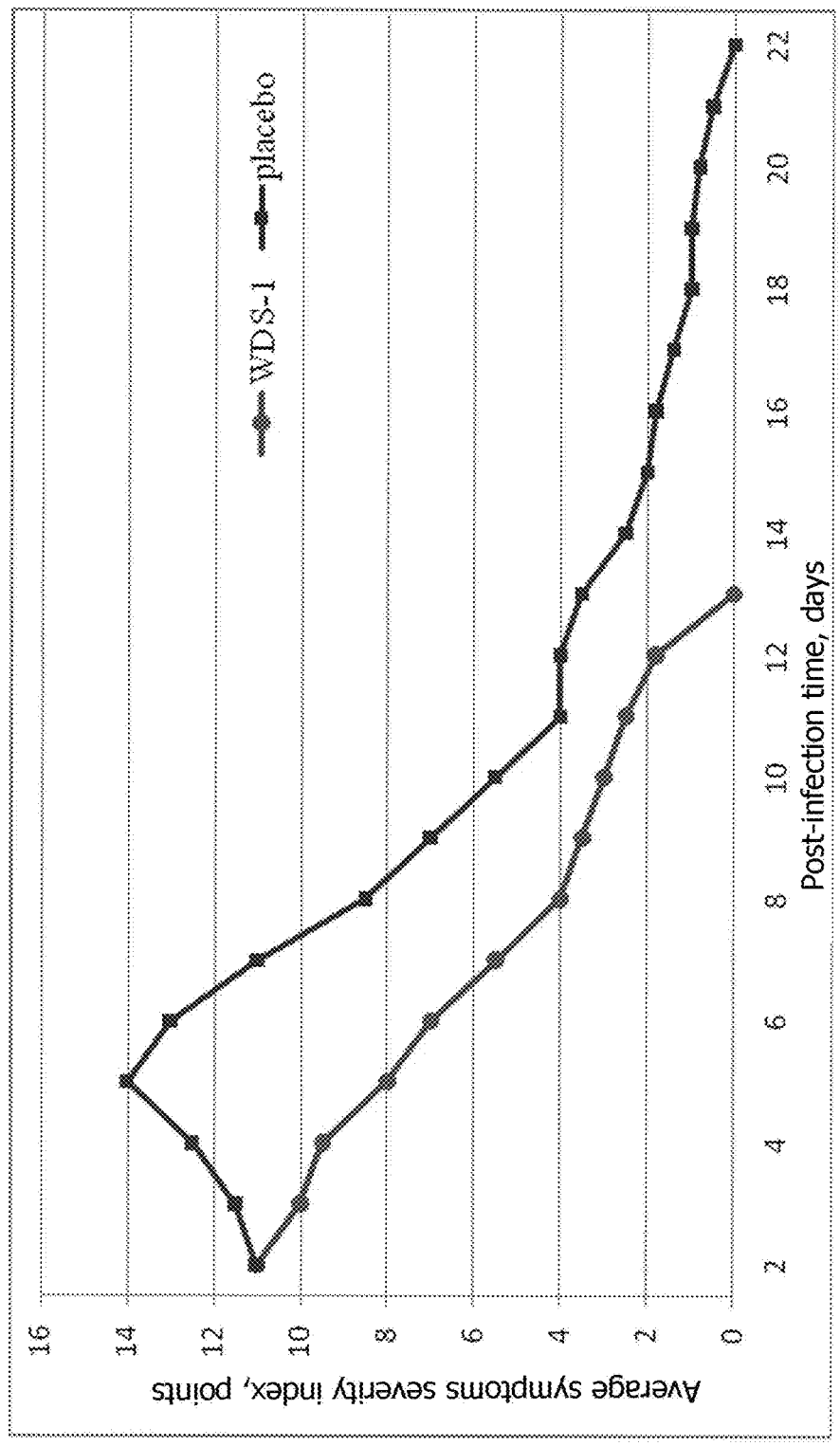

FIG. 5 shows the dynamics of ophthalmic herpes in rabbits. The therapeutic index for compound WDS-1 was 42.9%. In the group of rabbits treated with WDS-1, reduction in the severity of the inflammatory process was noticed as early as on 2nd treatment day, resulting in a rapid decrease of clinical manifestations. The activity of the agent manifested itself most rapidly in the treatment of epithelial keratitis. By 13th day post-infection, the clinical manifestations were attenuated. The survival of animals in the experimental group was 100% on the background of good tolerability against 66.7% in the control.

With WDS-1, viral isolates from eye swabs were noticed in animals only until 9 days post-infection, which was three days earlier than in the control group (Table 3).

TABLE 3

Effect of compound WDS-1 on HSV-1 reproduction in eye swab samples obtained from rabbits with ophthalmic herpes.

| No./No. | Group of animals | Post-infection time, days/Viral titers in animals with viral isolates, log $TCD_{50}$/0.1 mL(M ± m). | | | | |
|---|---|---|---|---|---|---|
| | | 2 | 5 | 7 | 9 | 12 |
| 1. | Control (placebo) | 2.75 ± 0.25 | 4.0 ± 0.25 | 2.75 ± 0.1 | 1.0 ± 0.1 | 0.5 ± 0.1 |
| 2. | "WDS-1" | 2.85 ± 0.25 | 1.25 ± 0.2 | 0.75 ± 0.1 | 0.5 ± 0.1 | 0 |

One can see from Table 3 that viral titer values isolated from animals that recieved WDS-1 on 5th day post-infection were significantly lower than the viral titers isolated from animals that recieved placebo; the respective values were 1.25 log $TCD_{50}$/0.1 mL against 4.0 log $TCD_{50}$/0.1 mL. High viral titers in control animals indicate the continuation of active virus reproduction, in particular in the corneal epithelium.

The results on the effect caused by the test compound on the frequency and level of HSV-1 reproduction in animals with viral isolates indicate that compound WDS-1 has a specific antiviral effect.

(b) Studies of the Immunostimulatory Activity of the Compounds According to the Invention.

Simultaneously with determining the effect of compound WDS-1 according to the invention on the course of induced herpetic eye infection in rabbits, we studied the production of specific virus-neutralizing antibodies (VAB) in an in vitro neutralization reaction in rabbits. Prior to the experiment, virus-neutralizing antibodies were absent in all animals. Fourteen days post-infection, the administration of the new substance in infected animals resulted in a significant increase in the induction of virus neutralizing antibodies (VAB). So, the control group animals had a neutralization index (NI), which shows the serum concentration of virus-neutralizing antibodies (VAB), of 2.0 log $TCD_{50}$, while in the infected animals on the background of WDS-1 administration, the neutralization index was 3.5 log $TCD_{50}$. A similar trend was observed in 21 days of observation.

Thus, our studies prove that the germanium complex compounds according to the invention have a combination mechanism of antiviral activity. Not only do they have an inhibitory effect on herpes viruses, including acyclovir-resistant strains (in particular HSV-1 "L2/R"), but they also simultaneously stimulate the formation and maintenance, for long periods of time, of a specific humoral immunity.

The germanium complex compounds according to the invention can be used for the treatment and prevention of diverse infections, in particular those caused by herpes viruses. Further, the germanium complex compounds according to the invention can be used as immunostimulatory agents. Thanks to the combination activity mechanism of the compounds according to the invention, therapeutic drugs comprising them would be efficient in the treatment and prophylaxis of immunocompromised persons, for example, AIDS patients, as well as cancer patients and those with organ transplants.

The newly prepared compounds are nontoxic and have good biopharmaceutical values, and thereby a wide spectrum of therapeutic drugs can be manufactured comprising, as an active component, the germanium complex compounds as claimed according to the invention in effective doses. The therapeutic drugs according to the invention can be embodied into diverse dosage forms: solid dosage forms (capsules, tablets), liquid dosage forms (solutions for infusion and for ingestion, eye drops), soft dosage forms (ointments, gels, suppositories), etc., and they can contain, as auxiliary components, pharmaceutically acceptable carriers and other commonly used ingredients.

The invention claimed is:

1. A germanium complex compound having the formula (I):

$$Ge_x[AD][CA]_y[AA]_z \qquad (I)$$

wherein AD is selected from the group consisting of acyclovir (9-[(2-hydroxyethoxy) methyl]guanine), valacyclovir (2-(guanin-9-ylmethoxy)ethyl L-valine ether), gancyclovir (9-[(1,3-dihydroxy-2-propoxy) methyl]guanine), pencyclovir (9-[4-hydroxy-3-(hydroxymethyl)butyl]guanine) and vidarabine (9-β-D-arabinofuranosyl adenine);
CA is a hydroxycarboxylic acid;
AA is an amino acid selected from the group consisting of arginine, glycine, lysine, and threonine,
wherein x=1-2, y=2-4, and z=0-2, and wherein
all CAs in the complex compound are the same or different, and
if present all AAs in the complex compound are the same or different.

2. The germanium complex compound according to claim 1, wherein the hydroxycarboxylic acid CA is selected from the group consisting of citric acid, lactic acid, malic acid, and mixtures thereof.

3. A pharmaceutical composition comprising, as an active component, a germanium complex compound according to claim 1 and at least one pharmaceutically acceptable carrier.

4. The germanium complex compound according to claim 1, wherein the AD is acyclovir, the hydroxycarboxylic acid CA is citric acid, and the amino acid AA is arginine.

5. A method for preparing a germanium complex compound according to claim 1, comprising the steps of:
 (a) mixing germanium dioxide with water to provide an aqueous solution or an aqueous slurry;
 (b) adding to said aqueous solution or said aqueous slurry:
  (i) a compound AD selected from the group consisting of acyclovir (9-[(2-hydroxyethoxy)methyl]guanine), valacyclovir (2-(guanin-9-ylmethoxy)ethyl L-valine ether), gancyclovir (9-[(1,3-dihydroxy-2-propoxy) methyl]guanine), pencyclovir (9-[4-hydroxy-3-(hydroxymethyl) butyl]guanine) and vidarabine (9-β-D-arabinofuranosyl adenine), at least one hydroxycarboxylic acid, and at least one amino acid selected from group consisting of arginine, glycine, lysine, and threonine;
 or
  (ii) a compound AD selected from the group consisting of acyclovir (9-[(2-hydroxyethoxy)methyl]guanine), valacyclovir (2-(guanin-9-ylmethoxy)ethyl L-valine ether), gancyclovir (9-[(1,3-dihydroxy-2-propoxy) methyl]guanine), pencyclovir (9-[4-hydroxy-3-(hydroxymethyl) butyl]guanine) and vidarabine (9-β-D-arabinofuranosyl adenine) and at least one hydroxycarboxylic acid,
wherein said components are added in any order;
 (c) heating the thus-obtained mixture under stirring at a temperature of 40-100° C. for 3-14 hours;
 (d) filtering the resulting solution; and
 (e) removing water from the solution to obtain a complex compound.

6. The method according to claim 5, wherein heating is carried out at a temperature of 80-100° C. for 5-12 hours.

7. The method according to claim 6, wherein heating is carried out at a temperature of 85-100° C. for 6-8 hours.

8. The method according to claim 5, wherein heating is carried out under stirring until a clear solution is formed.

9. The method according to claim 5, wherein the hydroxycarboxylic acid is selected from the group consisting of citric acid, lactic acid, malic acid, and mixtures thereof.

10. A method of treating a herpes I or II viral infection comprising administering to a host in need thereof an effective amount of the germanium complex compound of claim 1.

11. A pharmaceutical composition comprising, as an active component, a germanium complex compound according to claim 4 and at least one pharmaceutically acceptable carrier.

* * * * *